United States Patent [19]

Milani

[11] 4,218,467

[45] Aug. 19, 1980

[54] 8-METHOXY-3-PHENYL-5-METHYL-PROPARGYLAMINO-METHYL-2H-1 BENZOPYRAN-2-ONE AND PHARMACEUTICAL COMPOSITIONS CONTAIN IT

[75] Inventor: Davide Milani, Milan, Italy

[73] Assignee: Dott. Formenti S.p.A., Milan, Italy

[21] Appl. No.: 16,908

[22] Filed: Mar. 2, 1979

[30] Foreign Application Priority Data

Mar. 16, 1978 [GB] United Kingdom ............... 10421/78

[51] Int. Cl.$^2$ ..................... A61K 31/37; C07D 311/12
[52] U.S. Cl. .............................. 424/281; 260/343.44; 260/343.45
[58] Field of Search .................... 260/343.45; 424/281

[56] References Cited

FOREIGN PATENT DOCUMENTS 1426064 12/1965 France ................................ 260/343.45

OTHER PUBLICATIONS

Chemical Abstract vol. 76, Subject Index Guide, p. 203G.

Primary Examiner—Henry R. Jiles
Assistant Examiner—Jane T. Fan
Attorney, Agent, or Firm—Cushman, Darby & Cushman

[57] ABSTRACT

A novel anticonvulsive medicament, 8-methoxy-3-phenyl-5-methylpropargylaminomethyl-2H-1-benzopyran-2-one, is prepared starting from the (5-chloromethyl) homolog by subjecting the latter compound to refluxing with methylpropargylamine and to subsequent separations, extractions, acidifications and neutralization steps. The toxicity tests are satisfactory and the pharmacological assays encouraging.

3 Claims, No Drawings

8-METHOXY-3-PHENYL-5-METHYL-PROPARGYLAMINO-METHYL-2H-1 BENZOPYRAN-2-ONE AND PHARMACEUTICAL COMPOSITIONS CONTAIN IT

The subject-matter of the present invention is a novel compound which exhibits a marked activity, above all on the Central Nervous System (hereinafter indicated as CNS for short), said action being mainly an antinconvulsive activity.

The compounds according to the present invention has the following structural formula:

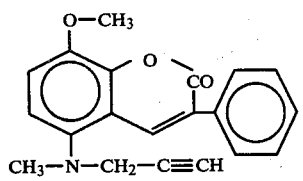

and its chemical name is 8-methoxy-3-phenyl-5-methyl-propargylaminomethyl-2H-1-benzopyran-2-one.

The compound of the formula (1) reported hereinabove can conveniently be prepared according to the following procedure:

8-methoxy-3-phenyl-2H-1-benzopyran-2-one is subjected, at the outset, to chloromethylation in a mixed acetic and hydrochloric environment, that is para-formaldehyde with gaseous hydrogen chloride, at a temperature of from 50° C. to 60° C. for a time from 3 to 4 hours. The reaction mixture is then poured in water and the solid which is thus separated is collected on a filter, washed with water and dried. The raw product which has thus been obtained is 8-methoxy-3-phenyl-5-chloromethyl-2H-1-benzopyran-2-one and is crystallized from an appropriate solvent, such as ethyl acetate and is condensed, in a benzene medium, with methylpropargylamine, in a ratio of 1 to 2 under refluxing conditions for 3 to 4 hours. The resultant reaction mixture is transferred into a separatory funnel, washed thoroughly with water, whereafter the organic phase is deprived of the water and evaporated. The residue is 8-methoxy-3-phenyl-5-methylpropargylaminomethyl-1,2-benzopyrone, that is, the expected compound of formula (1), and is crystallized from a appropriate solvent such as ligroin.

The usual salification procedures enable salts to be prepared of the compound of formula (1), such as the hydrochloride, the sulphate, the phosphate, the tartrate, the citrate, the maleate and others.

In order that the nature of this invention may be understood and carried to effect, a practical example of preparation will now be given hereinafter.

EXAMPLE

Preparation of the starting compound 8-methoxy-3-phenyl-5-chloromethyl-2H-1-benzopyran-2one.

30 grams of 8-methoxy-3-phenyl-2H-1-benzopyran-2-one are dissolved in 100 mls of acetic acid, whereafter 200 mls of conc.hydrochloric acid and 10 grams of paraformaldehyde are added thereto. Such reaction mixture is heated to 50° C.-60° C. and a stream of gaseous hydrogen chloride is caused to bubble therethrough. The mixture which has thus been obtained is now poured in water, the solid matter is collected on a filter, washed with water and dried. The raw product is crystallized from ethyl acetate and 26 grams of a crystalline product are obtained, the melting point of which is 158° C.-160° C.

For $C_{17}H_{13}ClO_3$. Calcd.: Cl% = 11.87. Found: Cl% = 11.76.

Final stage: Preparation of 8-methoxy-3-phenyl-5-methyl-propargylaminomethyl-2H-1-benzopyran-2-one.

25 grams of 8-methoxy-3-phenyl-5-chloromethyl-2H-1-benzopyran-2-one are dissolved in 200 mls benzene and 11.5 grams of methylpropargylamine are added thereto in the cold: the solution which is thus obtained is refluxed for 4 to 5 hours on a water-bath. The resultant reaction mixture is then poured in a separatory funnel, washed with water and extracted with a thrice-normal solution of sulphuric acid. The sulphuric-acid extracts are combined in a vessel and are cautiously alkalized with incremental pieces of solid potassium carbonate: the basic substance which is thereby separated is extracted with chloroform. The chloroform extract is washed with water, dried over anhydrous $MgSO_4$ and finally evaporated to dryness. The residue which is thus obtained is 8-methoxy-3-phenyl-5-methyl-propergylaminomethyl-2H-1-benzopyran-2-one, the expected compound of formula (1), and is crystallized from ligroin at 100° C.-150° C. There are obtained 12 grams of a crystalline solid which has a melting point of 137° C.-139° C.

| For $C_{21}H_{19}O_3N$ | | | |
|---|---|---|---|
| Calcd. | C % = 75.65 | H % = 5.74 | N % = 4.20 |
| Found | 75.78 | 5.81 | 4.50 |

The hydrochloride of (1) is a white crystalline solid melting at 178° C.-180° C.

| For $C_{21}H_{20}ClO_3N$ | | | | |
|---|---|---|---|---|
| | C % | H % | N % | Cl % |
| Calcd. | = 68.29 | = 5.42 | = 3.79 | = 9.62 |
| Found | 68.20 | 5.52 | 3.68 | 9.63 |

In order that the toxicological and pharmacological properties of the novel compound of the present invention may be fully appreciated, the data obtained from the appropriate tests on the same compound are reported hereinafter. In these tests, the active principle, that is the compound (1) of this invention has been preferably employed in the pharmaceutically acceptable form of its hydrochloride, which has been associated with pharmaceutically acceptable media.

Toxicological tests.

In mice, the values of the $LD_{50}$ of the product of formula (1) of this invention and relative to the intravenous administration route and the intraperitoneal route were 154 milligrams per kilogram b.w. and 4.0 grams per kilogram b.w. respectively.

The $LD_{50}$ for oral administration oscillates within the range which has been ascertained for the intraperitoneal administration, that is, an $LD_{50}$ of 3.75 grams per kg b.w. and this is a confirmation that the substance (1) is well absorbed orally.

In rats, the $LD_{50}$ which has been found has a value of 90 milligams per kilogram b.w. (body weight) intravenously.

The intraperitoneal toxicity is an $LD_{50}$ of from 5.0 to 10 grams.kg b.w. Post-mortem examination of rats which has received high doses of (1) has shown that deposits of such compound stagnated in the intraperitoneal cavity for 14 days without having been absorbed. There is, apparently, a limit for the amount of the compound which can be administered to such animal species and via the intraperitoneal route.

The compound (1) can thus be defined, on the basis of the tests reported above, a low-toxicity compound.

Pharmacological tests.

The toxicity tests reported above have shown that the compound (1) of this invention has an extremely low acute toxicity and it has also been regularly and repeatedly ascertained that the compound (1) reduces the spontaneous motive activity in mice but without inducing any general depression of the Central Nervous System. (CNS). The results of additional investigations have shown that such a type of activity has likewise been experienced with rats.

Further pharmacological tests have shown that the $ED_{50}$, i.e. the standard effective dose of (1) in rats was 33 milligrams/kg b.w., which is quite comparable with that of 33 milligrams/kg. b.w. in mice. In the behavioural tests intended to assay aggressivity and conditioned reactivity inhibition in mice, no such phenomena have ever been observed. It cannot be excluded, however, that further tests may reveal, in Primates, some behavioural modifications, but this will be the subject-matter of further studies.

The principal activity of the compound (1) is, as far as it has been ascertained now, a powerful anti-convulsive action.

Tests of anti-convulsive activity in mice have shown that the compound (1) is active in the supermaximal electroshock and also in the minimum electroshock threshold test. As a matter of fact, the $ED_{50}$ (effective dose) of (1) in the supermaximal electroshock was 46 milligrams/kg b.w., which is definitely a low value. In addition, if such a dose is compared with the oral $LD_{50}$ (lethal dose) in mice of 3.75 grams/kg b.w., this circumstance is such as to ensure that the compound (1) has an extremely satisfactory therapeutic index.

I claim:

1. A compound useful for the treatment of convulsive states, having the formula:

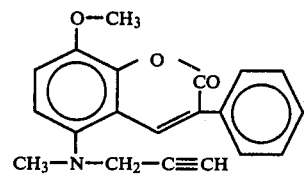

and the chemical name of which is 8-methoxy-3-phenyl-5-methylpropargylaminomethyl-2H-1-benzopyran-2-one.

2. A pharmaceutically acceptable acid addition salt of the compound as claimed in claim 1.

3. A pharmaceutical composition for the treatment of convulsive syndromes comprising a pharmaceutical carrier and an effective amount of the compound of claim 1 or a pharmaceutically acceptable acid addition salt thereof.

* * * * *